(12) United States Patent
Stürmer et al.

(10) Patent No.: US 8,399,225 B2
(45) Date of Patent: Mar. 19, 2013

(54) PROCESS FOR PREPARING URETHANE-CONTAINING (METH)ACRYLIC ESTERS

(75) Inventors: Rainer Stürmer, Rödersheim-Gronau (DE); Dejana Drew, Houston, TX (US); Bernhard Hauer, Fußgönheim (DE); Jürgen Däuwel, Heidelberg (DE); Uwe Meisenburg, Mannheim (DE)

(73) Assignee: BASF SE, Ludwigshafen (DE)

( * ) Notice: Subject to any disclaimer, the term of this patent is extended or adjusted under 35 U.S.C. 154(b) by 89 days.

(21) Appl. No.: 12/776,670

(22) Filed: May 10, 2010

(65) Prior Publication Data

US 2010/0291640 A1 Nov. 18, 2010

Related U.S. Application Data

(60) Provisional application No. 61/177,291, filed on May 12, 2009.

(30) Foreign Application Priority Data

May 12, 2009 (DE) .......................... 10 2009 003 035

(51) Int. Cl.
*C12P 7/60* (2006.01)
(52) U.S. Cl. ...................................................... 435/128
(58) Field of Classification Search .................. 435/128
See application file for complete search history.

(56) References Cited

U.S. PATENT DOCUMENTS 7,164,037 B2 * 1/2007 Dietsche et al. ............... 560/132
7,416,867 B2 * 8/2008 Haering et al. ............... 435/134

FOREIGN PATENT DOCUMENTS

JP 2001-40039 2/2001

OTHER PUBLICATIONS

Adam B. Hajjar, et al., "Preparation of Monomeric Acrylic Ester Intermediates Using Lipase Catalysed Transesterifications in Organic Solvents," Biotechnology Letters, vol. 12, No. 11, 1990, pp. 825-830.

Regina Derango, et al., "The Lipase-Catalyzed Synthesis of Carbamoyloxyethyl Methacrylate," Biotechnology Letters, vol. 16, No. 3, Mar. 1994, pp. 241-246.

* cited by examiner

*Primary Examiner* — Karen Cochrane Carlson
*Assistant Examiner* — Natalie Moss
(74) *Attorney, Agent, or Firm* — Oblon, Spivak, McClelland, Maier & Neustadt, L.L.P.

(57) ABSTRACT

The invention relates to a process for preparing urethane-containing acrylic- and (meth)acrylic esters by reacting a urethane-containing alcohol with a reactant acrylic- or (meth)acrylic ester of a saturated alcohol in the presence of at least one polymerization inhibitor and an enzyme as a catalyst within a reactor, wherein the saturated alcohol released in the process and optionally an entraining agent form an azeotrope with an excess of the reactant (meth)acrylic ester, such that the azeotrope is removed by distillation under reduced pressure and at least one substream from the bottom of the reactor is circulated through the top of the distillation column. Using this process, urethane-containing acrylic- and (meth)acrylic esters are prepared in high yields and high purities under mild conditions from economically obtainable reactants with no significant polymer formation.

15 Claims, No Drawings

PROCESS FOR PREPARING URETHANE-CONTAINING (METH)ACRYLIC ESTERS

The present invention relates to a process for preparing urethane-containing (meth)acrylic esters The preparation of (meth)acrylic esters is accomplished usually by acid- or base-catalyzed esterification or transesterification of (meth)acrylic acid or other (meth)acrylic esters with alcohols at temperatures of 40 to significantly more than 100° C. Owing to the high temperatures, the addition of high amounts of polymerization inhibitors is required in order to suppress undesired polymerization of the monomers. This often gives rise to complex and sometimes colored product mixtures. To remove discoloration and unconverted reactants, the product mixtures are worked up by inefficient alkaline scrubbing. The scrubbing process is laborious and costly, since partly esterified products in particular can be extracted and removed only slowly.

The preparation of urethane-containing (meth)acrylates via a conventional acid-catalyzed esterification is additionally difficult, since urethane groups are acid-sensitive.

JP 2001-40039 A describes carbamate-containing (meth) acrylic esters which are prepared via an acid-catalyzed esterification. A disadvantage of the process described is that the purity of the product obtained is only 75.9% with a mass balance of 95%.

EP 136 813 A2 describes the two-stage preparation of N-substituted, carbamate-containing acrylates by reaction of polyhydroxyalkylated acrylates with isocyanates. A disadvantage of the process described is the restriction to those substrates which are available as isocyanates. For example, N,N-disubstituted carbamates are not preparable by this process, and likewise those with N-substituents which bear isocyanate-reactive groups. For the reaction with isocyanate, toxic tin compounds are additionally needed as a catalyst.

The preparation of (meth)acrylic esters by an enzymatic esterification or transesterification is known.

Najjar et al. describe, in Biotechnol. Lett. 1990, 12, 825-830, the enzymatic transesterification of cyclic and open-chain alkanediols with ethyl acrylate with a lipase from *Chromobacterium viscosum*. The reactions proceed at an 18-fold molar excess of the alkyl acrylate over the diol in a solvent-free system. This gives rise to mixtures of mono- and diacrylates.

U.S. Pat. No. 5,240,835 describes the transesterification of alkyl acrylates with alcohols with catalysis by a biocatalyst from *Corynebacterium oxydans*. By way of example, the reaction of a 96-fold molar excess of ethyl acrylate with 2,2-dimethyl-1,3-propanediol is detailed there. Only 21% yield was obtained at 30° C. after 3 days.

Derango et al. describe, in Biotechnol. Lett. 1994, 16, 241-246, the lipase-catalyzed preparation of carbamoyloxy-ethyl methacrylate by transesterification of 2-hydroxyethyl carbamate with vinyl methacrylate. Complete conversion is achieved by virtue of the specific vinyl methacrylate reactant, since vinyl alcohol released is withdrawn from the reaction equilibrium as acetaldehyde. A disadvantage of this process is that vinyl methacrylate is not commercially available.

WO 2004/05088 A1 discloses a further enzyme-catalyzed preparation process for urethane-containing (meth)acrylic esters. A disadvantage of the process described is that the products have a relatively low purity and are nevertheless processed further in unpurified form.

It was therefore an object of the present invention to provide a further, alternative process with which urethane-containing (meth)acrylic esters are preparable in high yields and high purities from single, economically obtainable reactants.

The object is achieved by a process for preparing urethane-containing (meth)acrylic esters (U) by reacting a urethane-containing alcohol (A) with a (meth)acrylic ester of a saturated alcohol (G) in the presence of at least one polymerization inhibitor (P) with an enzyme (E) as a catalyst in a reactor, wherein a) the saturated alcohol released and any entraining agent used form an azeotrope with the excess corresponding (meth)acrylic ester (G), the azeotrope is removed by distillation under reduced pressure and b) at least a substream from the bottom of the reactor is circulated via the top of the distillation column.

With the aid of the process according to the invention, the preparation of urethane-containing (meth)acrylic esters is possible in high purity and high yields and under mild conditions. Moreover, no significant polymer formation occurs.

Urethane groups in the context of this document are O-substituted and N-unsubstituted, -monosubstituted or -disubstituted structural elements of the formula >N—C(=O)—O—.

(Meth)acrylic acid in this document represents methacrylic acid and acrylic acid, preferably acrylic acid.

"Saturated" in the context of this document means compounds without C—C multiple bonds (except, of course, the C=C double bond in the (meth)acryloyl units).

In the process according to the invention, a urethane-containing alcohol (A) is transesterified with a (meth)acrylic ester of a saturated alcohol (G) in the presence of at least one polymerization inhibitor (P) with an enzyme (E) as a catalyst, wherein, in accordance with the invention, the saturated alcohol released in the transesterification and any entraining agent used form an azeotrope with the excess corresponding (meth) acrylic ester (G), which is discharged under reduced pressure by means of a column attached to the reactor and then condensed. It is essential to the invention that at least a substream from the bottom of the reactor is circulated via the top of the distillation column.

According to the invention, the distillative removal of the azeotrope by means of a column attached to the reactor is effected under reduced pressure. The pressure is, for example, 20-700 mbar, preferably 30-500 mbar, more preferably 40-300 mbar and especially 50-150 mbar.

The azeotrope removed is subsequently condensed and advantageously fed directly into the plant for preparing the (meth)acrylic ester of a saturated alcohol (G), in order to reuse it there in the esterification with (meth)acrylic acid. If an entraining agent which is likewise removed as an azeotrope is additionally used, this entraining agent can first be removed from the azeotrope composed of saturated alcohol released and corresponding (meth)acrylic ester of a saturated alcohol (G), before the latter is supplied to the esterification with (meth)acrylic acid.

Additionally essential to the invention is the circulation of a substream from the bottom of the reactor via the top of the distillation column. The discharge of the bottom stream which is circulated via the top of the column is preferably not more than 50% by weight, based on the total weight of the bottom contents, preferably not more than 25% by weight, more preferably not more than 20% by weight and especially not more than 15% by weight.

The circulation of at least a substream from the bottom of the reactor prevents the unstabilized azeotrope from polymerizing in the column and blocking the top of the column. An additional addition of polymerization inhibitor to the distillation column can therefore advantageously be dispensed with in the process according to the invention.

Urethane-containing alcohols (A) are those compounds which comprise at least one urethane group, preferably 1 to 10 urethane groups, more preferably 1 to 5 urethane groups, even more preferably 1 to 2 urethane groups and especially one urethane group, and at least one hydroxyl group (—OH), preferably 1 to 10 hydroxyl groups, more preferably 1 to 6 hydroxyl groups, even more preferably 1 to 3 hydroxyl groups, particularly 1 to 2 hydroxyl groups and especially one hydroxyl group.

Preferred urethane-containing alcohols (A) have an average molar mass of 105 to 800 000 g/mol, preferably to 25 000 g/mol, more preferably to 5000 and most preferably to 4500 g/mol.

Particularly preferred urethane-containing alcohols (A) are those which are obtainable by
a) reacting an amine with a carbonate and
b) optionally purifying the reaction mixture obtainable from a).

Suitable amines for this reaction are ammonia, primary or secondary amines; carbonates are O,O'-disubstituted carbonates with the —O—C(=O)—O— structural element.

Very particularly preferred urethane-containing alcohols (A) are those which are obtainable according to the following reaction equation:

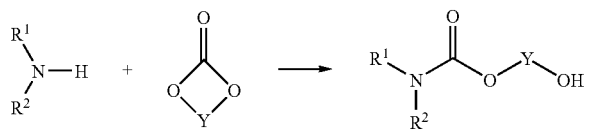

in which
$R^1$, $R^2$ are each independently hydrogen, $C_1$-$C_{18}$-alkyl, $C_2$-$C_{18}$-alkyl optionally interrupted by one or more oxygen and/or sulfur atoms and/or one or more substituted or unsubstituted imino groups, $C_2$-$C_{18}$-alkenyl, $C_6$-$C_{12}$-aryl, $C_5$-$C_{12}$-cycloalkyl or a five- or six-membered heterocycle having oxygen, nitrogen and/or sulfur atoms, where the radicals mentioned may each be substituted by aryl, alkyl, aryloxy, alkyloxy, heteroatoms and/or heterocycles, or a group of the formula —$[X_i]_k$—H, $X_i$ for each i=1 to k may independently be selected from the group of —$CH_2$—$CH_2$—O—, —$CH_2$—$CH_2$—N(H)—, —$CH_2$—$CH_2$—$CH_2$—N(H)—, —$CH_2$—CH($NH_2$)—, —$CH_2$—CH(NHCHO)—, —$CH_2$—CH($CH_3$)—O—, —CH($CH_3$)—$CH_2$—O—, —$CH_2$—C($CH_3$)$_2$—O—, —C($CH_3$)$_2$—$CH_2$—O—, —$CH_2$—$CH_2$—$CH_2$—O—, —$CH_2$—$CH_2$—$CH_2$—$CH_2$—O—, —$CH_2$—CHVin-O—, —CHVin-$CH_2$—O—, —$CH_2$—CHPh-O— and —CHPh-$CH_2$—O—, in which Ph is phenyl and Vin is vinyl, k is from 1 to 50 and Y is $C_2$-$C_{20}$-alkylene or $C_2$-$C_{20}$-alkylene interrupted by one or more oxygen and/or sulfur atoms and/or one or more substituted or unsubstituted imino groups and/or by one or more —(CO)—, —O(CO)O—, —(NH)(CO)O—, —O(CO)(NH)—, —O(CO)— or —(CO)O groups, where the radicals mentioned may each be substituted by aryl, alkyl, aryloxy, alkyloxy, heteroatoms and/or heterocycles.

$R^1$ and $R^2$ may also together form a ring.

$R^1$ and $R^2$ are preferably each independently hydrogen, $C_1$-$C_{12}$-alkyl, $C_5$-$C_6$-cycloalkyl or a group of the formula —$[X_i]_k$—H; $R^1$ and $R^2$ are more preferably each independently hydrogen, $C_1$-$C_4$-alkyl, $C_5$-$C_6$-cycloalkyl or a group of the formula —$[X_i]_k$—H, and even more preferably hydrogen, $C_1$-$C_4$-alkyl or a group of the formula —$[X_i]$k-H. In particular, one of the $R^1$ and $R^2$ radicals is hydrogen and the other is $C_1$-$C_4$-alkyl, or a group of the formula —$[X_i]_k$—H.

Preferred X, are —$CH_2$—$CH_2$—O—, —$CH_2$—$CH_2$—N(H)—, —$CH_2$—$CH_2$—$CH_2$—N(H)—, —$CH_2$—CH($NH_2$)—, —$CH_2$—CH(NHCHO)—, —$CH_2$—CH($CH_3$)—O— and —CH($CH_3$)—$CH_2$—O—, particular preference being given to —$CH_2$—$CH_2$—O—, —$CH_2$—$CH_2$—N(H)—, —$CH_2$—$CH_2$—$CH_2$—N(H)— and —$CH_2$—CH($NH_2$)— very particular preference to —$CH_2$—$CH_2$—O—, —$CH_2$—$CH_2$—N(H)— and —$CH_2$—$CH_2$—$CH_2$—N(H)—.

k is preferably 1 to 30, more preferably 1 to 20, even more preferably 1 to 10 and especially 1 to 5.

Examples of $R^1$ and/or $R^2$ are hydrogen, methyl, ethyl, isopropyl, n-propyl, n-butyl, isobutyl, sec-butyl, tert-butyl, n-hexyl, n-heptyl, n-octyl, n-decyl, n-dodecyl, n-tetradecyl, n-hexadecyl, n-octadecyl, n-eicosyl, 2-ethylhexyl, cyclopentyl, cyclohexyl, cyclooctyl, cyclododecyl, 2-hydroxyethyl, 2-hydroxypropyl, 1-hydroxypropyl, 5-hydroxy-3-oxapentyl, 8-hydroxy-3,6-dioxaoctyl or 11-hydroxy-3,6,9-trioxaundecyl.

Y is preferably $C_2$-$C_{10}$-alkylene, more preferably $C_2$-$C_6$-alkylene, even more preferably $C_2$-$C_4$-alkylene, particularly $C_2$-$C_3$-alkylene and especially $C_2$-alkylene, where the radicals mentioned may each be substituted by aryl, alkyl, aryloxy, alkyloxy, heteroatoms and/or heterocycles.

Examples of Y are 1,2-ethylene, 1,2-propylene, 1,1-dimethyl-1,2-ethylene, 1-hydroxymethyl-1,2-ethylene, 2-hydroxy-1,3-propylene, 1,3-propylene, 1,4-butylene, 1,6-hexylene, 2-methyl-1,3-propylene, 2-ethyl-1,3-propylene, 2,2-dimethyl-1,3-propylene and 2,2-dimethyl-1,4-butylene, preference being given to 1,2-ethylene, 1,2-propylene, 1,3-propylene, particular preference to 1,2-ethylene and 1,2-propylene and very particular preference to 1,2-ethylene.

Examples of amines include ammonia, methylamine, dimethylamine, ethylamine, diethylamine, isopropylamine, diisopropylamine, n-butylamine, di-n-butylamine, tert-butylamine, monoethanolamine, diethanolamine, propanolamine, dipropanolamine, piperidine, piperazine, pyrrolidine, cyclopentylamine, cyclohexylamine, aniline, ethylenediamine, diethylenetriamine, triethylenetetramine, tetraethylenepentamine and polymers with amine functions, as described in WO 04/050888 A1 at page 5 from line 28 to page 6 line 33.

Examples of carbonates include ethylene carbonate, 1,3-propylene carbonate and 1,2-propylene carbonate.

Preferred urethane-containing alcohols (A) are those compounds as disclosed in German published specification DE 10 2005 016 225 A1. Among the binary mixtures of structurally isomeric β-hydroxyalkyl carbamates specified therein, the isomer mixture of hydroxypropyl carbamate in particular is preferred for the process according to the invention. Hydroxypropyl carbamate is obtained by reaction of 1,2-propylene carbonate with ammonia according to DE 10 2005 016 255 A1.

The reaction of the amine with the carbonate is known per se, for example from U.S. Pat. No. 4,820,830 B, column 4 line 44 to column 5 line 9, and is not restricted.

Typically, the amine and the carbonate are reacted with one another in a stoichiometry of 0.7 to 1.2 mol of amine: 1 mol of carbonate, preferably 0.8-1.2:1, more preferably 0.9-1.1:1, even more preferably 0.95-1.1:1 and especially 1:1 mol/mol. The reaction is effected generally at a temperature of 0 to 120° C., particularly at 20 to 100° C., even more preferably 30 to 80° C. and even more preferably 40 to 80° C. The reaction has generally ended within 12 hours, preferably within 15 minutes to 10 hours, more preferably within 30 minutes to 8 hours, even more preferably 45 minutes to 6 hours and especially within 1 to 4 hours.

The total amine number to DIN 53176 of the urethane-containing alcohol (A) should not be more than 200 mg KOH/g preferably not more than 100 and most preferably not more than 80 mg KOH/g.

The reaction of the amine with the carbonate can be performed without solvent or in the presence of one, for example alcohols, ethers, ketones, hydrocarbons or water, preferably without solvent.

The urethane-containing alcohol (A) can be purified if desired in a further step, for example by filtration, distillation, rectification, chromatography, treatment with ionic exchangers, adsorbents, neutral, acidic and/or alkaline scrubbing, stripping or crystallization.

(Meth)acrylic esters of a saturated alcohol (G) are preferably those esters of (meth)acrylic acid with a saturated $C_1$-$C_{10}$-alcohol.

Examples of compounds (G) are methyl (meth)acrylate, ethyl (meth)acrylate, n-butyl (meth)acrylate, isobutyl (meth)acrylate, n-octyl (meth)acrylate, 2-ethylhexyl (meth)acrylate, 1,2-ethylene glycol di- and mono(meth)acrylate, 1,4-butanediol di- and mono(meth)acrylate, 1,6-hexanediol di- and mono(meth)acrylate, trimethylolpropane tri(meth)acrylate and pentaerythrityl tetra(meth)acrylate.

Particular preference is given to methyl (meth)acrylate, ethyl (meth)acrylate, n-butyl (meth)acrylate and 2-ethylhexyl (meth)acrylate, and very particular preference to methyl (meth)acrylate, ethyl (meth)acrylate and n-butyl (meth)acrylate.

Enzymes (E) usable in accordance with the invention are, for example, selected from hydrolases, esterases (E.C. 3.1.-.-), lipases (E.C. 3.1.1.3), glycosylases (E.C. 3.2.-.-) and proteases (E.C. 3.4.-.-) in free form or in chemically or physically immobilized form on a support, preferably lipases, esterases or proteases. Particular preference is given to Novozyme 435 (lipase from *Candida antarctica* B) or lipase from *Aspergillus* sp., *Aspergillus niger* sp., *Mucor* sp., *Penicilium cyclopium* sp., *Geotricum candidum* sp., *Rhizopus javanicus, Burkholderia* sp., *Candida* sp., *Pseudomonas* sp., or porcine pancreas, very particular preference being given to lipase from *Candida antarctica* B or from *Burkholderia* sp.

The enzyme content in the reaction medium is generally in the range from about 0.1 to 10% by weight, based on the sum of the components (A) and (G) used. The reaction time depends upon factors including the temperature, the amount used and the activity of the enzyme catalyst, and on the required conversion, and also on the urethane-containing alcohol (A). The reaction time is preferably adjusted such that the conversion of all hydroxyl functions originally present in the alcohol (A) is at least 70%, preferably at least 80%, more preferably at least 90%, even more preferably at least 95% and especially at least 97%. In general, 1 to 48 hours, preferably 1 to 12 hours and more preferably 1 to 6 hours are sufficient for that purpose.

The enzymatic transesterification with a (meth)acrylic ester of a saturated alcohol (G) is effected generally at 0 to 100° C., preferably 20 to 80° C., more preferably 20 to 70° C., most preferably 20 to 60° C.

The molar ratio of (meth)acrylic ester of a saturated alcohol (G) (based on the (meth)acryloyl units) to urethane-containing alcohol (A) (based on hydroxyl groups) may vary within a wide range, for example in a ratio of 100:1 to 1:1, preferably 50:1 to 1:1, more preferably 20:1 to 1:1 and most preferably 10:1 to 1:1. The (meth)acrylic ester of a saturated alcohol (G) is preferably present in a slight excess, which is distilled off with the alcohol released as an azeotrope under reduced pressure. In this way, the reaction equilibrium is shifted in favor of the urethane-containing (meth)acrylic ester (U).

Optionally, an entraining agent which forms an azeotrope with the saturated alcohol released and the corresponding excess (meth)acrylic ester (G) is additionally used. It is preferably an entraining agent whose azeotrope formed with the saturated alcohol released and the corresponding excess (meth)acrylic ester (G) exhibits phase separation or which can be broken by addition of water. Suitable entraining agents of this kind are, for example, n-pentane, n-hexane, n-heptane, cyclohexane, methylcyclohexane, benzene, toluene, xylene and any desired mixtures thereof.

The reaction may proceed in organic solvents or mixtures thereof or without addition of solvents. The mixtures are generally substantially anhydrous (i.e. addition of water less than 10, preferably less than 5, more preferably less than 1% by volume).

The proportion of organic solvents is, for example, 0.01-30% by weight, preferably 0.1-5% by weight. Suitable organic solvents are those known for these purposes, for example tertiary monools such as $C_3$-$C_6$-alcohols, preferably tert-butanol, tert-amyl alcohol, pyridine, poly-$C_1$-$C_4$-alkylene glycol di-$C_1$-$C_4$-alkyl ethers, preferably polyethylene glycol di-$C_1$-$C_4$-alkyl ethers, for example 1,2-dimethoxyethane, diethylene glycol dimethyl ether, polyethylene glycol dimethyl ether 500, $C_1$-$C_4$-alkylene carbonates, especially propylene carbonate, $C_3$-$C_6$-alkyl acetates, especially tert-butyl acetate, THF, toluene, 1,3-dioxolane, acetone, isobutyl methyl ketone, ethyl methyl ketone, 1,4-dioxane, tert-butyl methyl ether, cyclohexane, methylcyclohexane, toluene, hexane, dimethoxymethane, 1,1-dimethoxyethane, acetonitrile, and the mono- or polyphasic mixtures thereof.

Optionally, aqueous solvents can be added to the organic solvents, such that—according to the organic solvent—mono- or polyphasic reaction solutions arise. Examples of aqueous solvents are water and aqueous, diluted (e.g. 10 to 100 mM) buffers, for example with a pH in the range from 6 to 8, for example potassium phosphate or TRIS-HCl buffer.

The water content in the reaction mixture is generally 0-10% by volume. Preference is given to using the reactants without pretreatment (drying, water doping).

The substrates are present in the reaction medium in dissolved form, suspended as solids or in emulsion. The initial concentration of the reactants is preferably in the range from about 0.1 to 20 mol/l, especially 0.15 to 10 mol/l or 0.2 to 5 mol/l.

According to the invention, the reaction is performed batchwise. The reaction can be performed in all reactors suitable for such a reaction. Such reactors are known to those skilled in the art. Preference is given to effecting the reaction in a stirred tank reactor or a fixed bed reactor.

The distillation column attached to the reactor is of a design known per se and has the customary internals. Useful column internals include in principle all common internals, for example trays, structured packings and/or random packings. Among the trays, preference is given to bubble-cap trays, sieve trays, valve trays, Thormann trays and/or dual-flow trays; among the random packings, preference is given to those comprising rings, helices, saddles or braids. In general, 5 to 20 theoretical plates are sufficient.

The azeotrope distilled off is subsequently condensed in a condenser of conventional design.

To mix the reaction mixture, it is possible to use any processes. Specific stirrer apparatus is not required. The reaction medium may be mono- or polyphasic, and the reactants are dissolved, suspended or emulsified therein, initially charged optionally together with the molecular sieve and admixed with the enzyme preparation at the start of the reaction, and optionally once or more than once in the course of the reaction. The temperature is set to the desired value during the reaction and can, if desired, be increased or reduced during the course of the reaction.

When the reaction is performed in a fixed bed reactor, the fixed bed reactor is preferably equipped with immobilized enzymes, in which case the reaction mixture is pumped through a column filled with the enzyme. It is also possible to perform the reaction in a fluidized bed, in which case the enzyme is used immobilized on a support. The reaction mixture can be pumped continuously through the column, in which case the residence time and hence the desired conversion are controllable with the flow rate. It is also possible to pump the reaction mixture in circulation through a column, in which case the alcohol released or the azeotrope of alcohol released with the excess corresponding (meth)acrylic ester (G) and with any entraining agent used can also be distilled off simultaneously under reduced pressure.

After the reaction has ended, the reaction mixture obtainable can be used further without further purification, or it can be purified in a further step if required.

If the enzyme (E) used is not present immobilized in a fixed bed reactor or fluidized bed reactor, the enzyme used is generally merely removed from the reaction mixture, and the reaction product from any organic solvent used.

In such a case, a removal from the enzyme is effected, for example, by filtration, absorption, centrifugation or decantation. The enzyme removed can subsequently be used for further reactions.

The removal from the organic solvent is effected generally by distillation, rectification, or by filtration in the case of solid reaction products.

To further purify the reaction product, it is also possible to perform chromatography or a distillative purification.

If a distillative purification to purify the reaction product is performed, the urethane-containing (meth)acrylic ester (U) is isolated as the top product from the bottoms obtained in the optional solvent distillation in a further distillation step, and stabilized with at least one of the polymerization inhibitors specified below. Among the stabilizers specified there, especially hydroquinone monomethyl ether and phenothiazine are suitable for the distillative purification.

The rectification column usable for this distillation step is of known design, for example columns with random packing, columns with structured packing or tray columns, and has separating internals (e.g. bubble-cap, sieve or dual-flow trays) or comprises beds or ordered packings. These customary internals preferably have 10 to 20 theoretical plates. Thin-film evaporators are another option. Evaporators and condensers are likewise of conventional design.

The urethane-containing (meth)acrylic ester (U) is preferably obtained at a bottom temperature of 100-140° C., preferably of 110-130° C., and a top pressure of 1 to 100 mbar, preferably of 1 to 50 mbar, more preferably of 1 to 10 mbar and especially of 1 to 5 mbar.

For stabilization, a solution of 0.05-0.5% hydroquinone monomethyl ether or another similarly effective storage stabilizer can be sprayed into the condenser, the amount being selected such that the condensate has a storage stabilizer concentration of 10-20 ppm. A portion of the condensate, preferably 10-20%, can be fed back to the column as a return stream.

The urethane-containing (meth)acrylic ester (U) obtained has, according to gas chromatography analysis, a purity of at least 98.5%, preferably at least 99.0% and more preferably at least 99.5%.

The bottom product of the distillative purification, which consists principally of residual urethane-containing (meth) acrylic ester (U), Michael addition products, stabilizer and polymers, can be passed into a residue distillation and/or residue cleavage step.

It will be appreciated that it is also possible to combine the distillation units of the optional solvent distillation and the distillative purification. In this case, the pure urethane-containing (meth)acrylic ester (U) is discharged via a side draw, preferably in gaseous form, in the lower column region, preferably in the lower half, more preferably in the lower third, condensed and stabilized as described above.

In the purification step, however, preference is given to merely removing the enzyme used and any solvent used.

The reaction conditions in the enzymatic transesterification are mild. The low temperatures and otherwise mild conditions prevent the formation of by-products in the transesterification, which can otherwise originate, for example, from chemical catalysts or result from undesired free-radical polymerization of the (meth)acrylic ester (G) used, which can otherwise be prevented only by addition of stabilizers.

Since the (meth)acrylic ester of a saturated alcohol (G) used in the process according to the invention and the urethane-containing (meth)acrylic ester (U) are both polymerizable compounds, sufficient inhibition of polymerization has to be ensured in all process steps. Therefore, the transesterification, in accordance with the invention, takes place in the presence of at least one polymerization inhibitor (P). This may be the storage stabilizer present in any case in the (meth) acrylic ester (G), but it is also possible to add a further polymerization inhibitor.

In general, based on the unsaturated monomers, per individual substance, from 1 to 10 000 ppm, preferably from 10 to 5000 ppm, more preferably from 30 to 2500 ppm and especially from 50 to 1500 ppm of a suitable polymerization inhibitor (P) is used.

Suitable polymerization inhibitors (P) may, for example, be N-oxides (nitroxyl or N-oxyl radicals, i.e. compounds which have at least one >N—O•group), for example 4-hydroxy-2,2,6,6-tetramethylpiperidine N-oxyl, 4-oxo-2,2,6,6-tetramethylpiperidine N-oxyl, 4-acetoxy-2,2,6,6-tetramethylpiperidine N-oxyl, 2,2,6,6-tetramethylpiperidine N-oxyl, 4,4',4''-tris(2,2,6,6-tetramethylpiperidine N-oxyl) phosphite or 3-oxo-2,2,5,5-tetramethylpyrrolidine N-oxyl; mono- or polyhydric phenols which may have one or more alkyl groups, for example alkylphenols, for example o-, m- or p-cresol (methylphenol), 2-tert-butylphenol, 4-tert-butylphenol, 2,4-di-tert-butylphenol, 2-methyl-4-tert-butylphenol, 2-tert-butyl-4-methylphenol, 2,6-tert-butyl-4-methylphenol, 4-tert-butyl-2,6-dimethylphenol or 6-tert-butyl-2,4-dimethylphenol; quinones, for example hydroquinone, hydroquinone monomethyl ether, 2-methylhydroquinone or 2,5-di-tert-butylhydroquinone; hydroxyphenols, for example pyrocatechol (1,2-dihydroxybenzene) or benzoquinone; aminophenols, for example p-aminophenol; nitrosophenols, for example p-nitrosophenol; alkoxyphenols, for example 2-methoxyphenol (guaiacol, pyrocatechol monomethyl ether), 2-ethoxyphenol, 2-isopropoxyphenol, 4-methoxyphenol (hydroquinone monomethyl ether), mono- or di-tert-butyl-4-methoxyphenol; tocopherols, for example α-tocopherol and 2,3-dihydro-2,2-dimethyl-7-hydroxybenzofuran (2,2-dimethyl-7-hydroxycoumaran), aromatic amines, for example N,N-diphenylamine or N-nitrosodiphenylamine;

phenylenediamines, for example N,N'-dialkyl-p-phenylenediamine, where the alkyl radicals may be the same or different and each consist independently of from 1 to 4 carbon atoms and may be straight-chain or branched, for example N,N'-dimethyl-p-phenylenediamine or N,N'-diethyl-p-phenylenediamine, hydroxylamines, for example N,N-diethylhydroxylamine, imines, for example methyl ethyl imine or methylene violet, sulfonamides, for example N-methyl-4-toluenesulfonamide or N-tert-butyl-4-toluenesulfonamide, oximes, such as aldoximes, ketoximes or amide oximes, for example diethyl ketoxime, methyl ethyl ketoxime or salicylaldoxime, phosphorus compounds, for example triphenylphosphine, triphenyl phosphite, triethyl phosphite, hypophosphorous acid or alkyl esters of phosphorous acids; sulfur compounds, for example diphenyl sulfide or phenothiazine; metal salts such as copper or manganese, cerium, nickel, chromium salts, for example chlorides, sulfates, salicylates, tosylates, acrylates or acetates, for example copper acetate, copper(II) chloride, copper salicylate, cerium(III) acetate or cerium(III) ethylhexanoate, or mixtures thereof.

The polymerization inhibitor (mixture) used is preferably at least one compound from the group of hydroquinone, hydroquinone monomethyl ether, phenothiazine, 4-hydroxy-2,2,6,6-tetramethylpiperidine N-oxyl, 4-oxo-2,2,6,6-tetramethylpiperidine N-oxyl, 2-tert-butylphenol, 4-tert-butylphenol, 2,4-di-tert-butylphenol, 2-tert-butyl-4-methylphenol, 6-tert-butyl-2,4-dimethylphenol, 2,6-di-tert-butyl-4-methylphenol, 2-methyl-4-tert-butylphenol, hypophosphorous acid, copper acetate, copper(II) chloride, copper salicylate and cerium(III) acetate.

Very particular preference is given to using phenothiazine and/or hydroquinone monomethyl ether (MEHQ) as the polymerization inhibitor (P).

To further promote the stabilization, an oxygenous gas will preferably be present, preferably air or a mixture of air and nitrogen (lean air).

In a preferred embodiment, the process according to the invention makes it possible to obtain urethane-containing (meth)acrylic esters (U) of the formula (I)

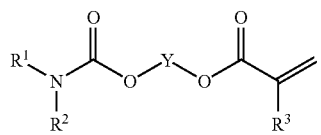

in which
R$^1$ and R$^2$ are each as defined above,
Y is selected from 1,2-ethylene, 1,2-propylene, 1,1-dimethyl-1,2-ethylene, 1-hydroxymethyl-1,2-ethylene, 2-hydroxy-1,3-propylene, 2-hydroxy-1,3-propylene, 1,3-propylene, 1,4-butylene, 1,6-hexylene, 2-methyl-1,3-propylene, 2-ethyl-1,3-propylene, 2,2-dimethyl-1,3-propylene and 2,2-dimethyl-1,4-butylene,
R$^3$ is hydrogen or methyl, preferably hydrogen,
with the proviso that at least one of the R$^1$ and R$^2$ radicals is not hydrogen.

One advantage of the process according to the invention is that substantially full conversions can be achieved with simple (meth)acrylic esters of saturated alcohols (G), since the reaction equilibrium can be shifted by the distillative removal of the azeotrope.

The urethane-containing (meth)acrylic esters (U) obtainable can advantageously be used as comonomers in poly(meth)acrylates or as reactive diluents in radiation-curable and/or dual-curable poly(meth)acrylates. Such poly(meth)acrylates are suitable as binders in radiation-curable or dual-curable coating materials. Coatings thus obtainable have very high scratch resistances, hardnesses, chemical stabilities, elasticity and adhesion, both on hydrophilic and on hydrophobic substrates.

A further use of the urethane-containing (meth)acrylic esters (U) prepared by the process according to the invention is as an additive in coating formulations. The urethane-containing (meth)acrylic esters (U) may be used either in basecoats or in topcoats. Owing to their exceptional properties, such as the increase in the scratch resistance and elasticity, and the lowering of the viscosity, especially in the case of branched polyacrylates, of a radiation-cured clearcoat, their use in topcoats is preferred.

For such a use, the urethane-containing (meth)acrylic ester (U) can suitably be blended with an addition of solvent, in order to prevent the solid state and to keep the urethane-containing (meth)acrylic ester (U) in the liquid phase. Suitable solvents for this purpose are lower hydrocarbons miscible therewith, such as methanol, ethanol, propanol, isopropanol, butanol, hexanol and any desired mixtures thereof. Typically, 0 to 40% by weight, preferably 5 to 30% by weight and more preferably 10 to 20% by weight of a suitable solvent is used, based in each case on the total weight of solvent and urethane-containing (meth)acrylic ester (U).

The examples which follow are intended to illustrate the properties of the invention, but without restricting them.

Unless stated otherwise, percent always means percent by weight and parts always mean parts by weight.

EXAMPLES

Example 1

Preparation of Hydroxypropyl Carbamate Acrylate

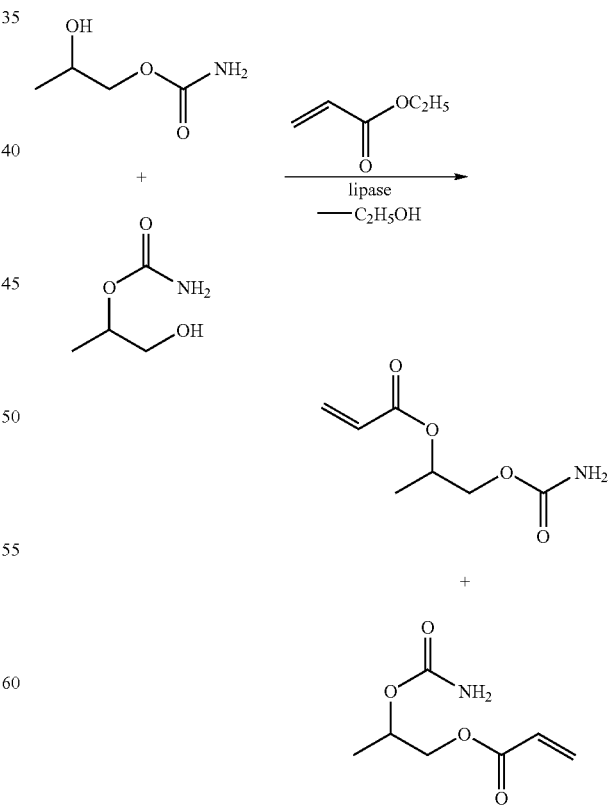

The transesterification of ethyl acrylate with hydroxypropyl carbamate was performed in a 400 l tank. This involved initially charging 17.8 kg of hydroxypropyl carbamate (isomer mixture) and 145.5 kg of ethyl acrylate, and also 12 g of hydroquinone monomethyl ether. The entire system was inertized with lean air (nitrogen/oxygen mixture with oxygen content 6%). The enzyme reactor connected in the external pumped circulation system comprised 1.3 kg of lipase (Novozym® 435). The reaction was performed at 40° C. and 90 mbar. The ethanol formed was distilled off continuously as an azeotrope with ethyl acrylate by means of a column (length l=150 cm, diameter d=20 cm, with Sulzer BX packing). Over the entire reaction time of 24 h, a stream of 5 kg/h from the tank bottoms was conducted via the top of the column in order to prevent polymerization.

The conversion was 90% after 24 h of reaction time. Subsequently, the crude product present in ethyl acrylate was washed twice with 1/10 each time of the total volume of water, which removed the unconverted reactant. The pure product obtained was hydroxypropyl carbamate acrylate in a purity of >95% (GC analysis).

Comparative Example 1

In a 4 l laboratory reactor, an analogous apparatus to example 1 was replicated on the 1:100 scale. 1/100 of the amounts specified in example 1 of each of the hydroxypropyl carbamate and ethyl acrylate reactants and of the methylhydroquinone monomethyl ether polymerization inhibitor and of the lipase (Novozym® 435) used as a catalyst were used. However, the bottoms discharge via the top of the column was dispensed with.

As early as after 6 h, the first polymer particles were detectable in the form of solid deposits at the top of the columns and on the packing of the column.

After 12 h, the reaction had to be stopped, since the upper part of the packing had become virtually impervious as a result of polymer.

The invention claimed is:

1. A process for preparing a urethane-containing (meth)acrylic ester product, the process comprising reacting a urethane-containing alcohol with a reactant (meth)acrylic ester of a saturated alcohol in the presence of at least one polymerization inhibitor and an enzyme as a catalyst in a reactor, wherein:

the saturated alcohol released in the process and optionally an entraining agent form an azeotrope with an excess of the reactant (meth)acrylic ester, such that the azeotrope is removed by distillation through a distillation column under reduced pressure; and at least one substream discharged from the bottom of the reactor is circulated through the top of the distillation column.

2. The process of claim 1, wherein the pressure of the distillation is 20-700 mbar.

3. The process of claim 2, wherein the pressure of the distillation is 30-500 mbar.

4. The process according to any one of the preceding claims, wherein enzymatic transesterification occurs at a temperature of 20-80° C.

5. The process according to any one of claims 1-3, wherein a molar ratio of the reactant (meth)acrylic ester to the urethane-containing alcohol is in the range from 50:1 to 1:1.

6. The process according to any one of claims 1-3, wherein an amount of the at least one substream circulated through the top of the distillation column is not more than 50% by weight, based on a total weight of contents in the bottom of the reactor.

7. The process of claim 6, wherein the amount of the at least one substream circulated through the top of the distillation column is not more than 25% weight.

8. The process according to any one of claims 1-3, wherein the urethane-containing alcohol is obtainable by the following reaction:

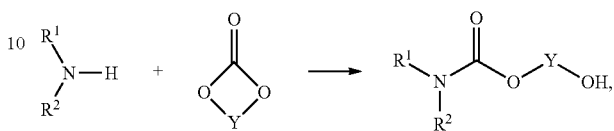

wherein:

$R^1$, $R^2$ are each independently hydrogen, $C_1$-$C_{18}$-alkyl, $C_2$-$C_{18}$-alkyl optionally interrupted by at least one selected from the group consisting of an oxygen atom, a sulfur atom, and a substituted or unsubstituted imino group, $C_2$-$C_{18}$-alkenyl, $C_6$-$C_{12}$-aryl, $C_5$-$C_{12}$-cycloalkyl, or a five- or six- membered heterocycle having at least one atom selected from the group consisting of oxygen, nitrogen, and sulfur, provided that a radical of $R^1$ and $R^2$ is optionally substituted by at least one group selected from the group consisting of an aryl group, an alkyl group, an group, an aryloxy group, a heteroatom group, a heterocycle group, and a group of formula —$[X_i]_k$—H;

$X_i$ for each i=1 to k is optionally and independently selected from the group —$CH_2$—$CH_2$—O—, —$CH_2$—$CH_2$—N(H)—, —$CH_2$—$CH_2$—$CH_2$—N(H)—, —$CH_2$—$CH(NH_2)$—, —$CH_2$—$CH(NHCHO)$—, —$CH_2$—$CH(CH_3)$—O—, —$CH(CH_3)$—$CH_2$—O—, —$CH_2$—$C(CH_3)_2$—O—, —$C(CH_3)_2$—$CH_2$—O—, —$CH_2$—$CH_2$—$CH_2$—O—, —$CH_2$—$CH_2$—$CH_2$—$CH_2$—O—, —$CH_2$—CHVin-O—, —CHVin-$CH_2$—O—, —$CH_2$—CHPh-O— and —CHPh-$CH_2$—O—, in which Ph is phenyl and Vin is vinyl;

k is from 1 to 50 and

Y is $C_2$-$C_{20}$-alkylene or $C_2$-$C_{20}$-alkylene interrupted by at least one group selected from the group consisting of an oxygen atom, a sulfur atom, a substituted or unsubstituted imino group a —(CO)— group, a —O(CO)O— group, a —(NH)(CO)O— group, a —O(CO)(NH)— group, a —O(CO)— group, and a —(CO)O group, wherein a radical of Y is optionally substituted by at least one group selected from the group consisting of an aryl group, an alkyl group, an aryloxy group, an alkyloxy group, a heteroatom group, and a heterocycle group.

9. The process according to any one of claims 1-3, wherein the reactant (meth)acrylic ester is selected from the group consisting of methyl (meth)acrylate, ethyl (meth)acrylate, n-butyl (meth)acrylate and 2-ethylhexyl (meth)acrylate.

10. The process according to any one of claims 1-3, wherein the enzyme is a lipase.

11. The process of claim 1, wherein, after the azeotrope is removed by distillation, the azeotrope is condensed and reused by feeding into the reactor.

12. The process of claim 1, comprising reacting the urethane-containing, alcohol with the reactant (meth)acrylic ester of a saturated alcohol in the presence of the at least one polymerization inhibitor, the enzyme, and an entraining agent, wherein the saturated alcohol released in the process and the entraining agent form an azeotrope with the excess of the reactant (meth)acrylic ester.

13. The process of claim 12, wherein, after the azeotrope is removed by distillation, the entraining agent is removed from the azeotrope before reactant (meth)acrylic ester contained in the azeotrope is supplied back to the reactor.

14. The process of claim 12, wherein the entraining agent is an agent whose azeotrope, which is formed with the saturated alcohol released in the process and the excess of the reactant (meth)acrylic ester, exhibits, phase separation or which can be broken by addition of water.

15. The process of claim 12, wherein the entraining agent is at least one selected from the group consisting of n-pentane, n-hexane, n-heptane, cyclohexane, methlcyclohexane, benzene, toluene, xylene, and mixtures thereof.

* * * * *